United States Patent [19]

Sherman

[11] Patent Number: 5,578,321

[45] Date of Patent: Nov. 26, 1996

[54] NEW CONTROLLED RELEASE FORMULATION OF DILTIAZEM HYDROCHLORIDE

[76] Inventor: Bernard C. Sherman, 50 Old Colony Rd., North York, Ontario, Canada, M2L 2K1

[21] Appl. No.: 439,383

[22] Filed: May 11, 1995

[30] Foreign Application Priority Data

May 11, 1994 [CA] Canada ................................ 2123332

[51] Int. Cl.⁶ ................................................ A61K 9/48
[52] U.S. Cl. ......................... 424/453; 424/451; 424/452; 424/456; 424/464; 424/465; 514/781
[58] Field of Search ................................ 424/453, 464, 424/465, 451, 452, 456

[56] References Cited

U.S. PATENT DOCUMENTS

| | | | |
|---|---|---|---|
| 4,839,177 | 6/1989 | Colombo et al. | 424/482 |
| 4,894,240 | 1/1990 | Geoghegan et al. | 424/497 |
| 5,000,962 | 3/1991 | Sangekar et al. | 424/482 |

*Primary Examiner*—James M. Spear
*Attorney, Agent, or Firm*—Nixon & Vanderhye P.C.

[57] ABSTRACT

A pharmaceutical tablet containing diltiazem hydrochloride suitable for once daily oral administration comprising by weight not less than 30 percent diltiazem hydrochloride and from 30 percent to 70 percent hydroxypropyl methylcellulose having a number average molecular weight of at least 50,000. A two piece hard gelatin capsule containing a plurality of such tablets.

8 Claims, No Drawings

NEW CONTROLLED RELEASE FORMULATION OF DILTIAZEM HYDROCHLORIDE

FIELD OF THE INVENTION

This invention relates to a controlled release pharmaceutical formulation of diltiazem hydrochloride suitable for once daily oral administration.

BACKGROUND OF THE INVENTION

Diltiazem is a benzothiazine derivative possessing calcium antagonist activity. Diltiazem blocks the influx of calcium ions in smooth and cardiac muscle and thus exerts potent cardio-vascular effects. Diltiazem has been shown to be useful in alleviating symptoms of chronic heart disease, particularly angina pectoris and myocardial ischemia and hypertension, while displaying a low incidence of side effects. The first dosage forms of diltiazem sold in the United States were tablets containing 30 mg or 60 mg of diltiazem hydrochloride sold under this tradename Cardizem by Marion Laboratories Inc. Single oral doses of 30 mg to 120 mg of Cardizem tablets result in peak plasma level about 2 to 3 hours after ingestion, and the elimination half-life is about 3 to 5 hours. Because of the relatively rapid absorption of diltiazem from such tablets and rapid elimination, the usual dosage regimen for such tablets is for the daily dosage to be taken in divided doses, three or four times daily. The need for such frequent administration may reduce patient compliance and produce irregular blood levels. Thus adverse therapeutic effects can arise. It thus became apparent that it would be preferable to administer diltiazem hydrochloride in a dosage form that releases the diltiazem hydrochloride much more slowly than Cardizem tablets, so as to enable the frequency of ingestion by the patient to be reduced from three or four times daily to once daily.

A dosage form of diltiazem hydrochloride that controls the rate of release to enable once daily administration is now sold in the United States under the trademark Cardizem CD, also by Marion Laboratories Inc. Cardizem CD is sold as capsules containing a multitude of pellets. The pellets are made using core seeds to which is applied a first coating containing the diltiazem hydrochloride. Over the first coating, further coatings of polymers are applied which serve to slow down and control the rate at which the diltiazem hydrochloride is released from the pellets in gastrointestinal fluids. The composition of the pellets contained in Cardizem CD capsules is described, in more detail in U.S. Pat. No. 4,894,240. While the formulation of Cardizem CD capsules successfully accomplishes gradual release to enable once daily administration, the procedures required to make and coat the pellets are time consuming and expensive.

Another formulation Of diltiazem hydrochloride suitable for once daily administration is sold in the United States under the tradename Dilacor XR by Rhone-Poulenc Rorer Pharmaceuticals Inc.

Dilacor XR is produced as two-piece hard gelatin capsules, with each capsule containing a multitude of tablets. The 180 mg strength of Dilacor XR contains three tablets and the 240 mg strength contains four tablets. The same tablets are used in both capsules, and each tablet contains 60 mg of diltiazem hydrochloride.

The tablets used in Dilacor XR are made in accordance with the invention of U.S. Pat. No. 4,839,177.

Each tablet weights about 205 mg and comprises of a cylindrical core containing diltiazem hydrochloride mixed with inactive ingredients which include a polymer that swells and forms a gel upon contact with aqueous fluids. Because the gel has high viscosity it swells and dissolves only very slowly in the gastrointestinal fluids to thereby retard the rate of release of the diltiazem hydrochloride. To further retard the release, insoluble polymeric platforms are affixed to the top and bottom of the cylindrical core, thus leaving only the periphery exposed to the gastrointestinal fluid. The formula of Dilacor XR capsules successfully accomplishes gradual release to enable once daily dosing, but, just as is the case with the Cardizem CD formulation, the Dilacor XR formulation requires complex and expensive procedures to produce. In particular, production of the tablets contained in Dilacor XR capsules requires production of cores containing the diltiazem hydrochloride and the affixing thereto of the insoluble platforms. Another difficulty with the Dilacor XR formulation is that the tablets are larger than desirable, so that the capsules containing 4 tablets must be size 00, which have an external diameter of about 8.5 mm and length of about 23.7 mm. These are difficult to, swallow because of this large size.

In view of the aforesaid problems with prior art formulations, it is an object of the invention to produce a dosage form of diltiazem hydrochloride with controlled release suitable for once daily administration, in the form of easy-to-make compressed tablets, and to make such tablets small enough such that four tablets, each containing 60 mg of diltiazem hydrochloride, can be contained within a gelatin capsule of size 0, which is a smaller size than size 00.

OUTLINE OF THE INVENTION

The new formulation is characterized in the following way. Diltiazem hydrochloride is mixed with a high molecular weight grade of hydroxypropyl methylcellulose, and optionally additional ingredients in relatively small quantities. The mix is made into granules, (either by conventional wet granulation and drying, or by the dry granulation methods known as slugging or compaction followed by milling), and the granules are made into tablets on a conventional tablet press. The diltiazem hydrochloride constitutes about 30 percent to 45 percent of the weight of the mix so that a tablet containing about 60 mg of diltiazem hydrochloride weighs about 135 mg. Using a tablet diameter of about 6.35 mm, the thickness of a tablet weighing about 135 mg is about 3.55 mm. Four such tablets will fit into a standard Size 0 capsule, providing a total of 240 mg diltiazem hydrochloride per capsule. With suitable selection of the hydroxypropyl methylcellulose within the scope of the invention, the dissolution rate of the tablets in gastrointestinal fluids is slow enough to make such tablets suitable for once daily administration.

To provide 180 mg per capsule, only three such tablets instead of four are placed within each gelatin capsule. Since a standard size 0 capsule will hold four tablets, capsules of less than standard length can be used for the 180 mg strength. Alternatively, a standard capsule can be used and left partly empty. Alternatively, a standard size 0 capsule can be used, and can be filled with three tablets containing each 60 mg diltiazem hydrochloride, and a fourth tablet being a placebo tablet of similar size but containing no diltiazem hydrochloride.

DETAILED DESCRIPTION OF THE INVENTION

A standard size 0 capsule has an internal diameter of about 7.1 mm. Accordingly, the maximum diameter of a cylindrical tablet to be placed within a size 0 capsule is about 6.5 mm to 7 mm. When fully closed, a standard size 0 capsule has an internal length of about 21 mm. However, the two ends of the capsules are rounded, and the length over which the fully closed capsule has the full internal diameter of about 7.1 mm is about 16 mm. Accordingly, if four cylindrical tablets are to be placed end to end within a size 0 capsule, the maximum thickness of each tablet is about one-quarter of 16 mm or 4 mm.

Size 0 capsules are also available in 'elongated' sizes; that is to say, capsules of the same diameter, but somewhat longer than standard. If size 0 elongated capsules are used, it is possible to enclose with such a capsule 4 tablets of diameter about 6.5 mm to 7 mm with the thickness of each tablet being somewhat higher than 4 mm, up to about 4.5 mm. A cylindrical tablet with diameter 7 mm and thickness 4 mm will have a weight of about 185 mg.

Accordingly, in order to fit 4 tablets into a standard size 0 capsule, the weight of each tablet cannot exceed about 185 mg. A tablet weight up to about 200 mg can be used by using elongated size 0 capsules. Since each tablet is to contain 60 mg diltiazem hydrochloride, it follows that the tablets must have a content of diltiazem hydrochloride of not less than about 30 percent by weight and preferably about 40 percent by weight, from which it follows that the content of inactive ingredients in the tablets (ie. ingredients other than the diltiazem hydrochloride) cannot be more than about 70 percent of the total tablet weight.

Diltiazem hydrochloride is highly and rapidly soluble in water. Thus in order to make tablets that release the diltiazem hydrochloride slowly enough to be suitable for once daily administration, it is necessary to include in the tablet an ingredient that will be very effective in slowing down dissolution. It must be sufficiently effective so that the amount required will not be more than about 70 percent of the weight of the tablet.

A suitable inactive ingredient for slowing the dissolution can be selected from the polymers known as hydroxypropyl methylcelluloses.

Hydroxypropyl methylcelluloses are available in various grades under several tradenames including Methocel E, F, J and K from the Dow Chemical Co., U.S.A. and Metolose SH from Shin-Etsu Ltd., Japan. The various grades available under a given tradename represent differences in methoxy and hydroxypropyl content as well as molecular weight and viscosity.

The viscosity of an aqueous solution of hydroxypropyl methylcellulose increases with increased number average molecular weight of the hydroxypropyl methylcellulose that is used. The number average molecular weight is the sum of the individual molecular weights of a representative sample population of molecules divided by the number of molecules.

When placed in aqueous media, such polymers hydrate to form a viscous gel. Accordingly, when such a polymer is included in the tablets along with the diltiazem hydrochloride, and a tablet is placed in aqueous media, the hydration of the polymer can cause a gel to be formed before any significant quantity of the diltiazem hydrochloride can dissolve. If the gel is sufficiently viscous, it will be dissolved away only very slowly, thus permitting the diltiazem hydrochloride to be dissolved and released only very slowly. In order to produce sufficient viscosity, the hydropropyl methylcelluloses that are used within the scope of the invention will have a number average molecular weight of at least 50,000. The preferred grades of hydroxypropyl methylcellulose within the scope of the invention are those that hydrate most rapidly and have relatively high number average molecular weights. In addition to the diltiazem hydrochloride and polymer, the mix used to form the tablets should also include a lubricant to prevent the mix from sticking to the tooling during tabletting. The lubricant used most commonly in the manufacture of pharmaceutical tablets is magnesium stearate, but other lubricants may be used. The mix may optionally contain other ingredients, such as a small amount of colloidal silicon dioxide as a gidant to make the mixed powder better flowing.

In order to convert the mixed powder into tablets on a conventional tablet press, the mixed powder must first be made into free flowing granules. This is done either by wet granulation or dry granulation methods. In the wet granulation method, the mix of diltiazem hydrochloride and the polymer is wet with water or another solvent to form a wet mass. The wet mass is then dried and ground into free flowing granules. The lubricant is then mixed in. In the dry mix process, the diltiazem hydrochloride, polymer and lubricant are mixed together and then compressed into large tablets or chips in a process known as slugging or compaction. These large tablets or chips are then ground up into free-flowing granules.

The free flowing granules (from either the wet granulation or dry granulation process) are then made into tablets on a conventional tablet press fitted with tooling to make tablets of the required diameter and adjusted to make tablets of the required weight and thickness. The weight of each tablet will be such as to contain 60 mg diltiazem hydrochloride per tablet.

To make 240 mg capsules, 4 such tablets will be filled into each size 0 capsule. To make 180 mg capsules, 3 such tablets will be filled into each size 0 capsule. The capsules used for the 180 mg strength will preferably be of shorter length such as to hold only 3 tablets. Alternatively, if standard capsules are used, and contain only 3 such tablets, the capsules will be partly empty. Alternately, if standard capsules are used, they can be filled with 3 tablets each containing 60 mg diltiazem hydrochloride and a fourth tablet being a placebo tablet of similar size but containing no diltiazem hydrochloride.

PREFERRED EMBODIMENT

In the preferred embodiment of the invention, each tablet contains 60 mg diltiazem hydrochloride. The diameter of the tablets is about 6.35 mm, the total weight per tablet is about 135 mg and the thickness of each tablet is about 3.6 mm so that 4 tablets substantially fill a standard size 0 capsule.

Apart from the diltiazem hydrochloride, the balance of the tablet weight is comprised mostly of hydroxypropyl methylcellulose.

In terms of the methyl and hydroxypropyl content, preferred grades of hydroxypropyl methylcellulose are those which hydrate most rapidly; these are grades having a methoxyl content of 16 to 24 weight percent, and a hydroxypropyl content of 4 to 32 weight percent. Particularly preferred is hydroxypropyl methylcellulose having a methoxyl content of 19 to 24 weight percent and a hydroxypropyl content of 4 to 12 weight percent, such as those sold under the tradename Methocel, known as type K. In terms of number average molecular weight, preferred grades are those with highest number average molecular weight so as to produce the highest viscosity from any given quantity.

The grade of Methocel type K with highest number average molecular weight presently commercially available is known as Methocel K100M. This grade has a number average molecular weight of above 150,000. Accordingly, Methocel K100M, is an especially preferred grade.

The most preferred mix also contains about 0.6% magnesium stearate as a lubricant, and about 0.15% colloidal silicon dioxide to make the mix better flowing. The mix is made into free flowing granules by the dry granulation process known as compaction. That is to say, the diltiazem hydrochloride, hydroxypropyl methylcellulose, magnesium stearate and colloidal silicon dioxide are mixed together as dry powders and then compacted into chips, which are then ground up to form small free flowing granules.

These granules are then made into tablets of about 6.35 mm diameter on a conventional tablet press. The tablet weight is about 135 mg containing about 60 mg diltiazem hydrochloride.

These tablets are filled into size 0 capsules as aforesaid; 4 such tablets per capsule for 240 mg capsules, and 3 such tablets per capsule for 180 mg capsules.

EXAMPLE 1

Ingredients were weighed out in the following proportions:

| | |
|---|---|
| diltiazem hydrochloride | 60.0 g |
| Methocel K100M | 74.0 g |
| magnesium stearate | .8 g |
| collodial silicon dioxide | .2 g |
| | 135.0 g |

The ingredients were mixed together and compacted, and the resulting chips ground into free flowing granules.

The granules were then compressed into cylindrical tablets of 6.35 mm diameter and 135 mg weight per tablet. The tablet thickness was about 3.6 mm.

Size 0 capsules were then filled with 4 tablets per capsule.

The dissolution rate of the capsules was then compared to Dilacor XR 240 mg capsules and found to be equivalent.

A comparative bioavailability study was then conducted in normal volunteers to compare the rate and extent of absorption of diltiazem hydrochloride from these capsules to that of Dilacor XR 240 mg capsules, and again the capsules were found to be equivalent.

What is claimed is:

1. A pharmaceutical composition suitable for once daily oral administration in the form of a two-piece hard gelatin capsule containing a plurality of tablets wherein each tablet has a diameter of less than 7.1 mm and comprises by weight from about 30 percent to about 50 percent diltiazem hydrochloride and from about 30 percent to 70 percent hydroxypropyl methylcellulose having a number average molecular weight of at least 50,000.

2. The pharmaceutical composition according to claim 1 wherein the number of tablets contained within the capsule is 3 or 4.

3. The composition according to claim 1 wherein the hydroxypropryl methylcellulose has a methoxyl content of 16 to 24 weight percent and a hydroxypropyl content of 4 to 32 weight percent.

4. The composition according to claim 3 wherein the hydroxypropyl methylcellulose has a number average molecular weight of at least 80,000.

5. The composition according to claim 3 wherein the hydroxypropyl methylcellulose has a number average molecular weight of at least 120,000.

6. The composition according to claim 1 wherein the hydroxypropyl methylcellulose has a methoxyl content of 19 to 24 weight percent and a hydroxypropyl content of 4 to 12 weight percent.

7. The composition according to claim 6 wherein the tablets comprise by weight from about 35 percent to about 45 percent diltiazem hydrochloride and from about 40 percent to about 65 percent hydroxpropyl methylcellulose.

8. The composition according to claim 1 wherein the capsule also contains an additional tablet that does not contain diltiazem hydrochloride.

* * * * *